United States Patent
Beckham et al.

(10) Patent No.: US 11,208,642 B2
(45) Date of Patent: Dec. 28, 2021

(54) MICROBIAL SYRINGOL UTILIZATION

(71) Applicants: Alliance for Sustainable Energy, LLC, Golden, CO (US); Montana State University, Bozeman, MT (US); University of Portsmouth, Portsmouth (GB)

(72) Inventors: Gregg Tyler Beckham, Golden, CO (US); Jennifer DuBois, Bozeman, MT (US); Melodie M. Machovina, Urbana, IL (US); Simon James Bradshaw Mallinson, Oxford (GB); John E. McGeehan, Portsmouth (GB); Christopher W. Johnson, Denver, CO (US); Alexander William Meyers, Denver, CO (US)

(73) Assignees: Alliance for Sustainable Energy, LLC, Golden, CO (US); Montana State University, Bozeman, MT (US); University of Portsmouth, Portsmouth (GB)

(*) Notice: Subject to any disclaimer, the term of this patent is extended or adjusted under 35 U.S.C. 154(b) by 0 days.

(21) Appl. No.: 16/684,206

(22) Filed: Nov. 14, 2019

(65) Prior Publication Data
US 2020/0199562 A1 Jun. 25, 2020

Related U.S. Application Data (60) Provisional application No. 62/767,264, filed on Nov. 14, 2018.

(51) Int. Cl.
*C12N 9/16* (2006.01)
*C12N 9/42* (2006.01)

(52) U.S. Cl.
CPC .................. *C12N 9/2437* (2013.01)

(58) Field of Classification Search
CPC ................ C12N 9/0002; C12N 9/2437
See application file for complete search history.

(56) References Cited

U.S. PATENT DOCUMENTS

2018/0023061 A1* 1/2018 Neidle ............... C12N 9/0071
435/142

OTHER PUBLICATIONS

Johnson et al., "Aromatic Catabolic Pathway Selection for Optimal Production of Pyruvate and Lactate from Lignin", Metabolic Engineering, Mar. 2015, vol. 28, pp. 240-247.
Tumen-Velasquez et al., "Accelerating pathway evolution by increasing the gene dosage of chromosomal segments", Proceedings of the National Academy of Sciences of the United States of America, Jul. 2018, vol. 115, No. 27, pp. 7105-7110.
Machovina et al., "Enabling microbial syringol utilization through structure-guided protein engineering", Proceedings of the National Academy of Sciences of the United States of America, Jul. 2019, vol. 116, No. 28, pp. 13970-13976.

* cited by examiner

*Primary Examiner* — Tekchand Saidha
(74) *Attorney, Agent, or Firm* — Sam J. Barkley (57) ABSTRACT

Disclosed herein are compositions of non-naturally occurring enzymes to enable microbial syringol utilization with GcoAB.

9 Claims, 7 Drawing Sheets

Specification includes a Sequence Listing.

MTTTERPDLAWLDEVTMTQLERNPYEVYERLRAEAPLAFVPVLGSYVASTAEVCREVATS
PDFEAVITPAGGRTFGHPAIIGVNGDIHADLRSMVEPALQPAEVDRWIDDLVRPIARRYL
ERFENDGHAELVAQYCEPVSVRSLGDLLGLQEVDSDKLREWFAKLNRSFTNAAVDENGEF
ANPEGFAEGDQAKAEIRAVVDPLIDKWIEQPDDSAISHWLHDGMPPGQTRDREYIYPTIY
VYLLGAMQEPGHGMASTLVGLFSRPEQLEEVVDDPTLIPRAIAEGLRWTSPIWSATARIS
TKPVTIAGVDLPAGTPVMLSYGSANHDTGKYEAPSQYDLHRPPLPHLAFGAGNHACAGIY
FANHVMRIALEELFEAIPNLERDTREGVEFWGWGFRGPTSLHVTWEV

FIG. 7

SEQUENCE LISTING

<160> NUMBER OF SEQ ID NOS: 1

<210> SEQ ID NO 1
<211> LENGTH: 407
<212> TYPE: PRT
<213> ORGANISM: Artificial Sequence
<220> FEATURE:
<223> OTHER INFORMATION: cytochrome P450 mutant protein CYP255A

<400> SEQUENCE: 1

Met Thr Thr Thr Glu Arg Pro Asp Leu Ala Trp Leu Asp Glu Val Thr
1               5                   10                  15

Met Thr Gln Leu Glu Arg Asn Pro Tyr Glu Val Tyr Glu Arg Leu Arg
                20                  25                  30

Ala Glu Ala Pro Leu Ala Phe Val Pro Val Leu Gly Ser Tyr Val Ala
            35                  40                  45

Ser Thr Ala Glu Val Cys Arg Glu Val Ala Thr Ser Pro Asp Phe Glu
50                  55                  60

Ala Val Ile Thr Pro Ala Gly Gly Arg Thr Phe Gly His Pro Ala Ile
65                  70                  75                  80

Ile Gly Val Asn Gly Asp Ile His Ala Asp Leu Arg Ser Met Val Glu
                85                  90                  95

Pro Ala Leu Gln Pro Ala Glu Val Asp Arg Trp Ile Asp Asp Leu Val
            100                 105                 110

Arg Pro Ile Ala Arg Arg Tyr Leu Glu Arg Phe Glu Asn Asp Gly His
        115                 120                 125

Ala Glu Leu Val Ala Gln Tyr Cys Glu Pro Val Ser Val Arg Ser Leu
    130                 135                 140

Gly Asp Leu Leu Gly Leu Gln Glu Val Asp Ser Asp Lys Leu Arg Glu
145                 150                 155                 160

Trp Phe Ala Lys Leu Asn Arg Ser Phe Thr Asn Ala Ala Val Asp Glu
                165                 170                 175

Asn Gly Glu Phe Ala Asn Pro Glu Gly Phe Ala Glu Gly Asp Gln Ala
            180                 185                 190

Lys Ala Glu Ile Arg Ala Val Val Asp Pro Leu Ile Asp Lys Trp Ile
        195                 200                 205

Glu Gln Pro Asp Asp Ser Ala Ile Ser His Trp Leu His Asp Gly Met
    210                 215                 220

Pro Pro Gly Gln Thr Arg Asp Arg Glu Tyr Ile Tyr Pro Thr Ile Tyr
225                 230                 235                 240

Val Tyr Leu Leu Gly Ala Met Gln Glu Pro Gly His Gly Met Ala Ser
                245                 250                 255

Thr Leu Val Gly Leu Phe Ser Arg Pro Glu Gln Leu Glu Glu Val Val
            260                 265                 270

Asp Asp Pro Thr Leu Ile Pro Arg Ala Ile Ala Glu Gly Leu Arg Trp
        275                 280                 285

Thr Ser Pro Ile Trp Ser Ala Thr Ala Arg Ile Ser Thr Lys Pro Val
    290                 295                 300

Thr Ile Ala Gly Val Asp Leu Pro Ala Gly Thr Pro Val Met Leu Ser
305                 310                 315                 320

Tyr Gly Ser Ala Asn His Asp Thr Gly Lys Tyr Glu Ala Pro Ser Gln
                325                 330                 335

Tyr Asp Leu His Arg Pro Pro Leu Pro His Leu Ala Phe Gly Ala Gly
            340                 345                 350

Asn His Ala Cys Ala Gly Ile Tyr Phe Ala Asn His Val Met Arg Ile

```
                355                 360                 365
Ala Leu Glu Glu Leu Phe Glu Ala Ile Pro Asn Leu Glu Arg Asp Thr
    370                 375                 380

Arg Glu Gly Val Glu Phe Trp Gly Trp Gly Phe Arg Gly Pro Thr Ser
385                 390                 395                 400

Leu His Val Thr Trp Glu Val
                405
```

MICROBIAL SYRINGOL UTILIZATION

CROSS-REFERENCE TO RELATED APPLICATION

This application claims priority under 35 U.S.C. § 119 to U.S. Provisional Patent Application No. 62/767,264 filed on 14 Nov. 2018, the contents of which are hereby incorporated by reference in their entirety.

CONTRACTUAL ORIGIN

The United States Government has rights in this invention under Contract No. DEAC36-08GO28308 between the United States Department of Energy and the Alliance for Sustainable Energy, LLC, the Manager and Operator of the National Renewable Energy Laboratory.

SEQUENCE LISTING

The instant application contains a Sequence Listing which has been submitted via EFS-web and is hereby incorporated by reference in its entirety. The ASCII copy as filed herewith was originally created on 13 Mar. 2020. The ASCII copy as filed herewith is named NREL 18-135_ST25.txt, is 4 kilobytes in size and is submitted with the instant application.

BACKGROUND

Lignin is a heterogeneous, recalcitrant biopolymer that is prevalent in plant cell walls, where it provides structure, defense against pathogens, and water and nutrient transport through plant tissue. Lignin is synthesized primarily from three aromatic building blocks, making it an abundant and renewable aromatic carbon feedstock available. Due to its recalcitrance, rot fungi and some bacteria have evolved powerful, oxidative enzymes that deconstruct lignin to smaller fragments. Once broken down, the lignin oligomers can be assimilated as a carbon and energy source through at least four known aromatic-catabolic pathways.

In most plants, lignin is comprised primarily of coniferyl (G) and sinapyl (S) alcohol monomers, which have either one or two methoxy groups on the aryl ring, respectively. Nearly all lignin-derived aromatics require O-demethylation of these methoxy groups as an essential step in their conversion to central intermediates.

Together, G- and S-lignin are the major components of lignin in hardwoods and grasses, with their relative amounts dependent upon the plant species. Due to their abundance, it is of great interest to find enzymes that can act on the methoxy groups of both G- and S-lignin subunits. There are no reports describing syringol O-demethylation or more broadly, even its catabolism by microbes.

A reaction in the aerobic conversion of lignin-derived compounds is O-aryl-demethylation, which occurs on methoxylated lignin-derived compounds to produce diols such as catechol, protocatechuate (3,4-dihydroxybenzoate), and gallate (3,4,5-trihydroxybenzoate). The diol rings are cleaved by dioxygenases, in either an extra- or intradiol manner, and then funneled into central carbon metabolism where they can be used as a carbon and energy source. Harnessing this catabolic capability for the conversion of heterogeneous lignin streams into valuable chemicals is of keen interest for the development of viable lignin valorization strategies, an essential need for lignocellulose conversion.

SUMMARY

In an aspect, disclosed is a non-naturally occurring GcoAB enzyme capable of O-aryl-demethylation of syringol.

In another aspect, disclosed is a method for the degradation of lignin a step of which includes the use of a non-naturally occurring GcoAB enzyme capable of O-aryl-demethylation of syringol.

In an aspect, a non-naturally occurring organism capable of expressing an engineered GcoAB enzyme capable of O-aryl-demethylation of syringol.

In an aspect disclosed is a non-naturally occurring GcoAB enzyme capable of the O-aryl-demethylation of syringol and the O-aryl-demethylation of guaiacol. In an embodiment, the enzyme has a phenylalanine at the active site has been changed to alanine. In an embodiment, the enzyme has a $k_{cat}$ for guaiacol of at least 11 sec$^{-1}$ and a $k_{cat}$ for syringol of at least 5.9 sec$^{-1}$. In an embodiment, the enzyme has a $K_M$ for guaiacol of less than about 40 mM and a $K_M$ for syringol of less than about 10 mM. In another embodiment, the enzyme has a $k_{cat}/K_M$ for guaiacol of greater than about 290 mM$^{-1}$ sec$^{-1}$ and a $k_{cat}/K_M$ for syringol of greater than about 600 mM$^{-1}$ sec$^{-1}$. In an embodiment, the enzyme has increased specific activity for guiaicol when compared to the native GcoAB enzyme. In an embodiment, the enzyme has an amino acid that is selected from the group consisting of alanine, serine, histidine, valine, isoleucine, and leucine. In an embodiment, the enzyme has a specific activity for syringol is greater than 0.54 µmol sec$^{-1}$ µmol$^{-1}$. In an embodiment, the enzyme has a specific activity for syringol is greater than 3.9 µmol sec$^{-1}$ µmol$^{-1}$. In an embodiment, the enzyme has a specific activity for syringol is greater than 5.1 sec$^{-1}$.

In an aspect, disclosed is a method for the degradation of lignin comprising the use of a non-naturally occurring GcoAB enzyme capable of O-aryl-demethylation of syringol and the O-aryl-demethylation of guaiacol. In an embodiment, the method includes the use of a non-naturally occurring GcoAB enzyme comprises a phenylalanine at the active site that has been changed to an amino acid that allows the non-naturally occurring enzyme to use both guaiacol and syringol as a substrate. In an embodiment, the method uses an enzyme that has an amino acid is selected from the group consisting of alanine, serine, histidine, valine, isoleucine, and leucine.

In an aspect, disclosed is an organism comprising a non-naturally GcoAB enzyme capable of the O-aryl-demethylation of syringol and the O-aryl-demethylation of guaiacol. In an embodiment, the organism uses an enzyme that comprises a phenylalanine at the active site has been changed to alanine.

BRIEF DESCRIPTION OF THE DRAWINGS

FIG. 5A depicts conservation of residues within 6 Å of guaiacol in GcoA (PDB code 5NCB). Conservation scores are reported as percentiles. GcoA-F169 is the least conserved in this region. FIG. 5B depicts the frequency of amino acids occurring at position 169 among GcoA homologs.

FIG. 6A depicts two pathways that were tested for in vivo syringol conversion. The pathway in orange leads to syringol conversion to 3MC and cleavage to 2-hydroxymuconate 6-methyl ester, whereas the second pathway in purple allows for O-demethylation to pyrogallol and cleavage to 2-pyrone 6-carboxylate. FIG. 6B depicts the results after 6 hours when the strains were analyzed for their ability to turn over syringol via $^1$H NMR spectroscopy. Syringol (green) is completely converted to pyrogallol (red), 3MC (blue), or 6-pyrone 6-carboxylate (purple) in AM157.

DETAILED DESCRIPTION

Microbial conversion of aromatic compounds is a promising strategy for valorization of the plant biopolymer lignin. An often rate-limiting reaction in aromatic catabolism is O-aryl-demethylation of the abundant aromatic methoxy groups in lignin to form diols, which enables subsequent oxidative aromatic ring-opening. Recently, a cytochrome P450 system, GcoAB, was discovered to demethylate guaiacol (2-methoxyphenol), the simplest aromatic component of coniferyl alcohol-derived lignin, to form catechol. GcoAB consists of a cytochrome P450 protein from the family CYP255A (GcoA) and a three-domain reductase (GcoB). Native GcoAB has minimal ability to demethylate syringol (2,6-dimethoxyphenol), the analogous building block for sinapyl alcohol-derived lignin, for which no pathway for syringol catabolism has been reported, despite the abundance of sinapyl alcohol-based lignin in plants.

Disclosed herein are exemplary embodiments of the invention that provide an engineered two-component cytochrome P450 enzyme system to catalyze aromatic O-demethylation of syringol, the base aromatic unit of S-lignin.

GcoAB is a two-component P450 enzyme system that demethylates several diverse aromatic compounds including guaiacol (the simplest G-type lignin subunit), guaethol, anisole, 2-methylanisole, and 3-methoxycatechol (3MC) with similar or greater efficiency than other O-aryl-demethylases. However, GcoAB has poor reactivity towards syringol, the simplest S-type lignin subunit.

Native GcoA does not catalyze syringol O-demethylation. Crystallographic studies and molecular dynamics (MD) simulations indicated that a triad of active site phenylalanine residues is both highly motile and important for positioning of the substrate into its catalytically competent pose. As disclosed herein, the substitution of GcoA-F169, which has the closest interaction with the bound substrate, relaxes the specificity of the enzyme sufficiently to permit the O-demethylation of S-lignin type substrates. Disclosed herein are non-naturally occurring GcoA enzymes, such as GcoA-F169, that are capable of highly efficient in vitro and in vivo syringol turnover, and where the enzyme also retains highly efficient activity against guaiacol.

In an embodiment, disclosed herein are non-naturally occurring GcoAB enzymes that were engineered to enable microbial syringol utilization. In an embodiment, a phenylalanine residue (GcoA-F169) was identified that interferes with the binding of syringol in the active site, and upon mutation to smaller amino acids, efficient syringol O-demethylation is achieved.

Analysis of the crystallographic model indicated that syringol adopts a productive binding pose in the engineered GcoA-F169 variant, which molecular dynamics simulations traced to the elimination of steric clash between the highly flexible side chain of GcoA-F169 and the additional methoxy group of syringol. Also disclosed herein is in vivo syringol turnover in Pseudomonas putida KT2440 with the GcoA-F169A GcoA mutant. Thus, the significant potential and plasticity of cytochrome P450 aromatic O-demethylases in the biological conversion of lignin-derived aromatic compounds are demonstrated in preferred embodiments as disclosed herein.

Engineering GcoA Mutants

The syringol binding mode can be modulated by active site engineering. Guaiacol assumes a productive orientation in the active site of GcoA due to the action of amino acid side chains that create a tight-fitting hydrophobic pocket. The closest contact is with GcoA-F169, which forms a hydrophobic interaction with the C6 carbon on the aromatic ring of guaiacol. MD simulations suggest that this residue is highly mobile, predicting that the productive complex forms dynamically. Superposition of the co-crystal structures of GcoA with guaiacol and syringol reveals a shift in the positions of GcoA-F169 and the reactive syringol methoxy group relative to the heme. Functionally, these shifts in the GcoA-F169 position permit both strong binding of syringol ($K_D$=2.8±0.4 µM) and stimulation of NADH consumption, though without substantial syringol turnover. We identified that the mutation of GcoA-F169 to a smaller residue may relieve the apparent steric clash between it and the bound ligand in the active site, allowing syringol to adopt a productive conformation. To test this hypothesis, GcoA-F169 was substituted with several alternative amino acids (A, S, H, V, I, and L) with the aim of introducing productive syringol turnover while retaining reactivity with guaiacol.

Crystallization screens of the resulting proteins with both ligands were set up. The successful generation of a set of four syringol-bound structures (F169A with syringol, F169H with syringol, F169S with syringol, and F169V with syringol) provided direct insight into the minimal reduction in side-chain bulk required to achieve a putative productive binding mode. A step-wise trajectory of the bound syringol towards the optimum orientation with decreasing side-chain bulk was observed in the superposition of four co-crystal structures, confirming the choice of GcoA-F169 as a productive target. Specifically, GcoA-F169H creates an improved substrate orientation, further improved by GcoA-F169V, and essentially optimized in both the GcoA-F169S and F169A proteins. Indeed, a comparison of the GcoA-F169A-syringol structure with the wild-type (WT) guaiacol structure reveals an almost perfect alignment relative of the aromatic rings of each substrate. The GcoA-F169A mutant has a highly similar measured affinity for guaiacol, syringol, and the singly methoxylated species 3MC (see FIG. 3). Without being bound by theory, the translation and rotation achieved by releasing the steric clash imposed by GcoA-F169 allows the positioning of the reactive methoxy group in optimum position for catalysis, as judged by comparison to the WT-guaiacol ligand-bound structure and DFT-optimized transition states.

Each protein variant (F169A, F169H, F169I, F169L, F169S, F169V) also crystallized successfully with guaiacol and the structures showed that the orientation of the bound ligand remained consistent with that of the WT enzyme. Even the largest reduction in side-chain bulk, represented by the GcoA-F169A variant, retained the ideal reactive geometry for the natural substrate. Furthermore, comparison of the surrounding active site architecture confirmed no significant deviation from the WT. The resolution of these structures (1.66-2.17 Å) also provides sufficient electron density quality to explore changes in the hydration of the pocket. While the native enzyme excluded water from the active site pocket, we were interested to see if this was maintained when a new cavity in the pocket was introduced. The syringol bound mutants, A, S, and V contain an additional ordered water in the active site which may help to maintain the substrate in a productive binding pose for catalysis. The bulkier GcoA-F169H mutant excludes water from the active site, as with the WT structure. Taken together, the substrate orientation in these crystal structures indicates that several of the mutants might be able to accommodate both guaiacol and syringol in a potentially productive manner.

GcoA-F169A Efficiently Demethylates Both Guaiacol and Syringol with Only Limited Uncoupling Models generated through crystallographic techniques suggested that several mutants might be able to accommodate both guaiacol and syringol in a productive manner. Substrate analogs are also known to stimulate the P450 reaction with NADH/$O_2$ without concomitant oxygenation of the organic substrate. This leads to uncoupling of NADH, substrate oxidation, and $H_2O_2$ production.

Figure 1A:
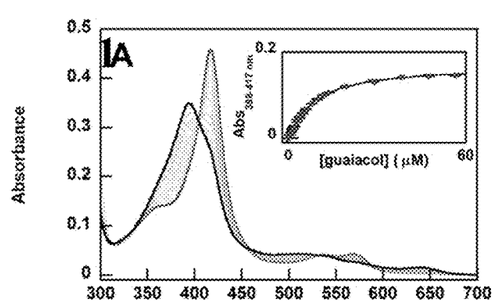
FIG. 1A depicts binding of both guaiacol and syringol shows a spin state change in GcoA-F169A and comparable $K_D$s.
Figure 1B:
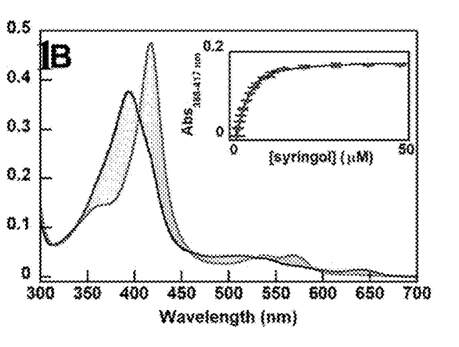
FIG. 1B depicts binding of both guaiacol and syringol shows a spin state change in GcoA-F169A and comparable $K_D$s.
Figure 1C:
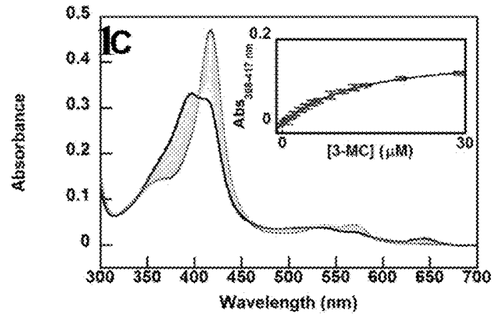
FIG. 1C depicts binding of both guaiacol and syringol shows a spin state change in GcoA-F169A and comparable $K_D$s. Guaiacol (FIG. 1A) caused the Soret peak (λ=417 nm) of GcoA-F169A to shift to 387 nm, indicating the conversion of a low-spin to a high-spin species. Syringol (FIG. 1B) caused the Soret peak (λ=417 nm) of GcoA-F169A to shift to 387 nm, indicating the conversion of a low-spin to a high-spin species. 3MC (FIG. 1C) caused the Soret peak (λ=417 nm) of GcoA-F169A to shift to 387 nm, indicating the conversion of a low-spin to a high-spin species. 0-60 µM substrate was titrated into a solution containing 3 µM GcoA-F169A and air-saturated buffer (25 mM HEPES, 50 mM NaCl, pH 7.5, 25° C.) and the spectra monitored until there was no more change, indicating saturation. The solution reached equilibrium prior to each substrate addition. $AbS_{388-417}$ nm was plotted against the concentration of substrate and fit to the quadratic equation for weakly binding ligands to obtain values for $K_D$: guaiacol=7.1±0.1 µM, syringol=1.7±0.07 µM, and 3MC=9.5±0.02 µM. Error bars represent ±1 standard deviation of two or more runs.
Figures 2A, 2B:
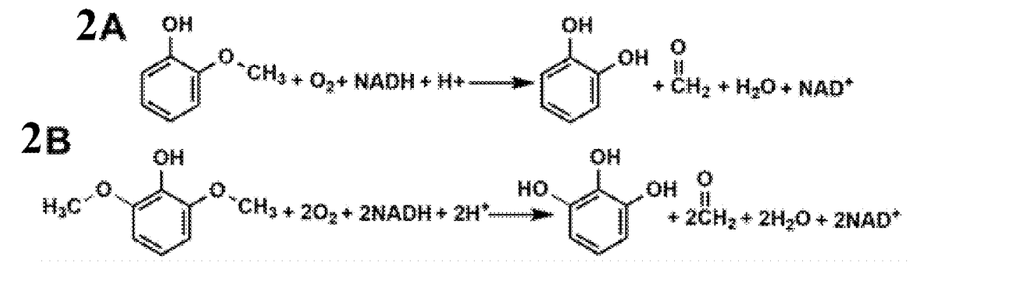
FIG. 2A depicts O-demethylation of guaiacol to form catechol and formaldehyde.
FIG. 2B depicts demethylation of syringol to form pyrogallol and two formaldehydes.

To address whether guaiacol and/or syringol would serve as substrates of GcoA-F169A, the disappearance of NADH (UV/vis) and aromatic substrate (HPLC) was monitored over time (FIG. 1). The rates of organic substrate and NADH consumption were robust and the same within error, regardless of whether guaiacol or syringol was used (5.3±0.3 µM guaiacol $s^{-1}$ µmol GcoA-F169A$^{-1}$, 5.8±0.8 µM NADH $s^{-1}$ µmol GcoA-F169A-1; 4.1±0.3 µM syringol $s^{-1}$ µmol GcoA-F169A$^{-1}$, 5.1±0.8 µM NADH $s^{-1}$ µmol GcoA-F169A$^{-1}$). This suggests that both guaiacol and syringol serve as substrates for GcoA-F169A.

The oxidative O-demethylation of guaiacol moreover appeared to be largely coupled to NADH consumption. When NADH and $O_2$ were present in excess of guaiacol, the measured stoichiometry of the GcoA-F169A-catalyzed reaction was very close to one molecule each of guaiacol and NADH consumed to one formaldehyde and one catechol produced (FIG. 1), without overconsumption of NADH (91±8% coupling efficiency, Table 1).

TABLE 1

Rates of substrate disappearance and coupling efficiencies for reactions catalyzed by the GcoA-F169A variant.

| GcoA variant | syringol | | guaiacol | | 3MC | |
|---|---|---|---|---|---|---|
| | Specific activity (µmol sec$^{-1}$ µmol$^{-1}$ GcoA)$^a$ | Coupling efficiency (%)$^b$ | Specific activity (µmol sec$^{-1}$ µmol$^{-1}$ GcoA)$^a$ | Coupling efficiency (%)$^b$ | Specific activity (µmol sec$^{-1}$ µmol$^{-1}$ GcoA)$^a$ | Coupling efficiency (%)$^b$ |
| WT | n/a | 7.1 ± 0.8 | 5.0 ± 0.1 | 110 ± 10 | 3.2 ± 0.2 | 78 ± 3 |
| F169A | 5.1 ± 0.8 | 104 ± 6 | 5.8 ± 0.8 | 103 ± 7 | 5.6 ± 0.8 | 68 ± 20 |
| F169S | 5.1 ± 0.9 | 85 ± 5 | 5.7 ± 0.8 | 67 ± 8 | 6.0 ± 0.8 | 67 ± 8 |
| F169H | 3.9 ± 0.2 | 56 ± 7 | 7.9 ± 3 | 103 ± 10 | 4.3 ± 0.4 | 28 ± 20 |
| F169V | 4.1 ± 0.8 | 100 ± 10 | 5.3 ± 0.2 | 105 ± 2 | 5.7 ± 0.3 | 40 ± 3 |
| F169I | 0.56 ± 0.2 | 14 ± 2 | 1.4 ± 0.2 | 41 ± 10 | 1.1 ± 0.7 | 10 ± 9 |
| F169L | 0.54 ± 0.1 | 7.8 ± 2 | 4.5 ± 0.3 | 73 ± 3 | 0.57 ± 0.2 | 5.0 ± 4 |

The [a] in Table 1 notes that NADH consumption was monitored continuously over time via UV/vis and quantifying with ε340=6.22 mM$^{-1}$ cm$^{-1}$ at 25° C., 25 mM HEPES, 50 mM NaCl, pH 7.5 and saturating (200 μM) concentrations of all substrates (syringol, guaiacol, and 3MC). The [b] in Table 1 notes that the values were calculated as the molar ratio of formaldehyde produced per NADH consumed in a fixed-time assay. Assay conditions: 0.2 μM GcoA variant, 0.2 μM GcoB, 200 μM NADH, 100 μg/mL catalase, 200 μM aromatic substrate in 25 mM HEPES, 50 mM NaCl, pH 7.5, 25° C., 210 μM O$_2$.

Since both methoxy groups of syringol can potentially serve as substrates, we examined syringol turnover in a number of ways. Syringol (100 μM) was first incubated with NADH (200 μM) and excess dissolved O$_2$ (210 μM), and the reaction with the GcoA-F169A mutant allowed to go to completion. As with the guaiacol reaction, all of the NADH and syringol were consumed (FIG. 3), implying that syringol undergoes two O-demethylations, producing 3MC and then pyrogallol (210 μM O$_2$, 25 mM HEPES, 50 mM NaCl, pH 7, 25° C.). However, less than the expected formaldehyde (170±10 μM) was produced, suggesting some uncoupling of NADH/O$_2$ consumption from the oxidative O-demethylation. Consistent with that hypothesis, 50±4 μM of the singly demethylated intermediate 3MC was observed at the end of the reaction, even though sufficient NADH/O$_2$ were present to enable its complete conversion to pyrogallol. Notably, pyrogallol was not detected under any of the conditions used here, possibly due to its instability in the presence of O$_2$.

The stoichiometric analysis was next repeated with NADH and syringol present in equal concentrations (200 μM each; 210 μM O$_2$), conditions expected to permit at most half of the available methoxy groups to react. All of the NADH and 150±6 μM of syringol were consumed; 200±3 μM formaldehyde and 120±2 μM 3MC were generated (Table 1, FIG. 3). The accumulation of roughly half an equivalent of 3MC (relative to NADH) under these conditions suggested that the first O-demethylation of syringol is faster than the second, and that the uncoupling reaction was likely stimulated by 3MC rather than by syringol. Consistent with those expectations, the rate of 3MC disappearance measured by HPLC was significantly slower than the disappearance of either guaiacol or syringol (2.6±0.3 μM 3MC s$^{-1}$ μmol GcoA-F169A$^{-1}$, 5.6±0.8 μM NADH s$^{-1}$ μmol GcoA-F169A$^{-1}$); moreover, the faster consumption of NADH relative to 3MC suggested diminished reaction coupling (64±10% coupling, Table 2).

TABLE 2

The GcoA-F169A variant efficiently demethylates guaiacol and syringol.

| | WT[a] | | GcoA-F169A[a] | |
|---|---|---|---|---|
| | guaiacol | syringol | guaiacol | syringol |
| k$_{cat}$ (sec$^{-1}$) | 6.8 ± 0.02 | n/a | 11 ± 0.03 | 5.9 ± 0.01 |
| K$_M$ (mM) | 60 ± 10 | n/a | 40 ± 6 | 10 ± 1 |
| k$_{cat}$/K$_M$ (mM$^{-1}$ sec$^{-1}$) | 110 ± 20 | n/a | 290 ± 40 | 600 ± 90 |

The [a] in Table 2 notes that 0.2 μM GcoAB was reacted with 100 μg/mL catalase, 300 μM NADH, and 0-300 μM substrate, 25° C., 25 mM HEPES, 50 mM NaCl, pH 7.5, 210 μM O$_2$.

Figure 3:
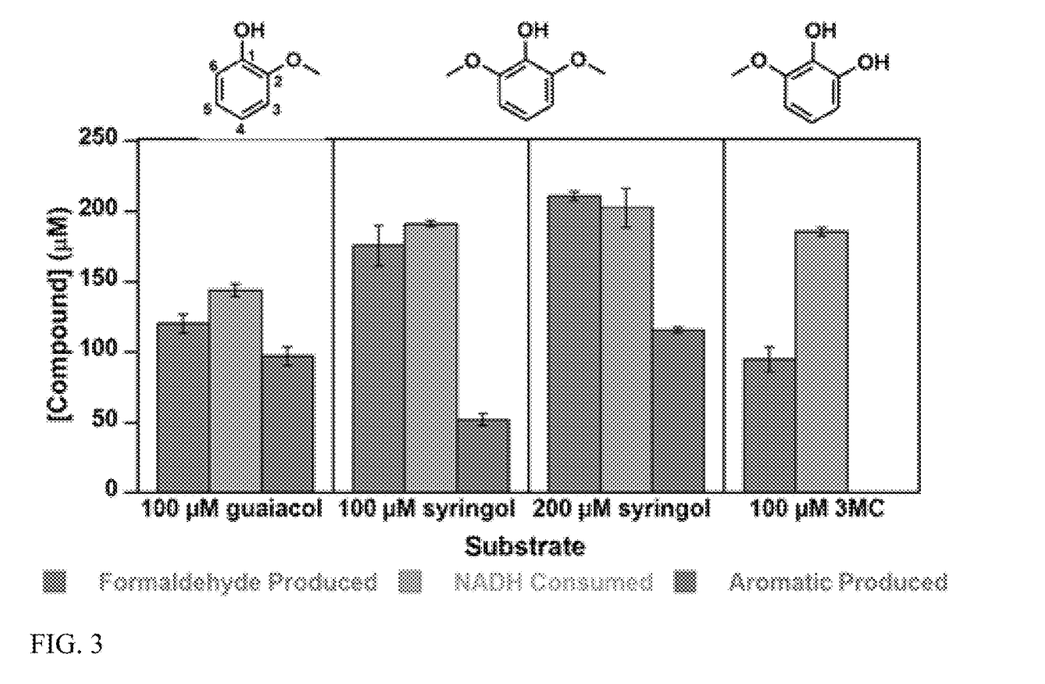
FIG. 3 depicts quantitative analyses of substrate consumption and product generation indicate nearly complete coupling of $NADH/O_2$ consumption to substrate O-demethylation for guaiacol, and progressively more uncoupling for syringol and 3MC. NADH (200 µM) and guaiacol, syringol, or 3MC (100 or 200 µM) were incubated in air with 0.2 µM GcoA-F169A and GcoB (each) (25 mM HEPES, 50 mM NaCl, pH 7.5, 25° C., 210 µM $O_2$). Reactants and products were quantified when the UV/vis spectra ceased changing and the reaction deemed complete. The total NADH consumed is compared above to the amounts of formaldehyde and de-methylated aromatic compound produced. Pyrogallol, the O-demethylated product of 3MC, was not detected under any condition. Error bars represent ±1 standard deviation from three or more independent measurements.

In reactions containing 100 μM of 3MC and 200 μM NADH, the majority of the initially available NADH was consumed, and approximately 100 μM of formaldehyde was produced (FIG. 3). The observed overconsumption of NADH was due to the uncoupled reaction, which could lead to H$_2$O$_2$ production. The production of H$_2$O$_2$ in the presence of excess NADH/O$_2$ and limiting 3MC was confirmed using Amplex Red and horseradish peroxidase (Table 3).

TABLE 3

Uncoupling reactions with GcoA-F169A and guaiacol, syringol, or 3MC.

| Substrate | % Formaldehyde produced[a] | % H$_2$O$_2$ produced[b] |
|---|---|---|
| guaiacol + 100 μM NADH | 100 ± 10 | 3.7 ± 0.6 |
| syringol + 100 μM NADH | 125 ± 6 | 7.4 ± 0.03 |
| syringol + 200 μM NADH | 91 ± 8 | 7.9 ± 0.5 |
| 3-MC + 100 μM NADH | 52 ± 7 | 17 ± 0.2 |

The [a] in Table 3 notes that 0.2 μM GcoA-F169A and GcoB were reacted with 100 μg catalase, 100 or 200 μM NADH, and 100 μM substrate in 25 mM HEPES, 50 mM NaCl, pH 7.5, 25° C., 210 μM O$_2$. Endpoint analyses were done to quantify formaldehyde produced, which was then referenced to NADH consumed. The [b] in Table 3 notes that the same reaction done above was repeated to quantify H$_2$O$_2$ produced using the Amplex Red/HRP assay. The amount of hydrogen peroxide was then referenced to NADH consumed.

Figure 4:
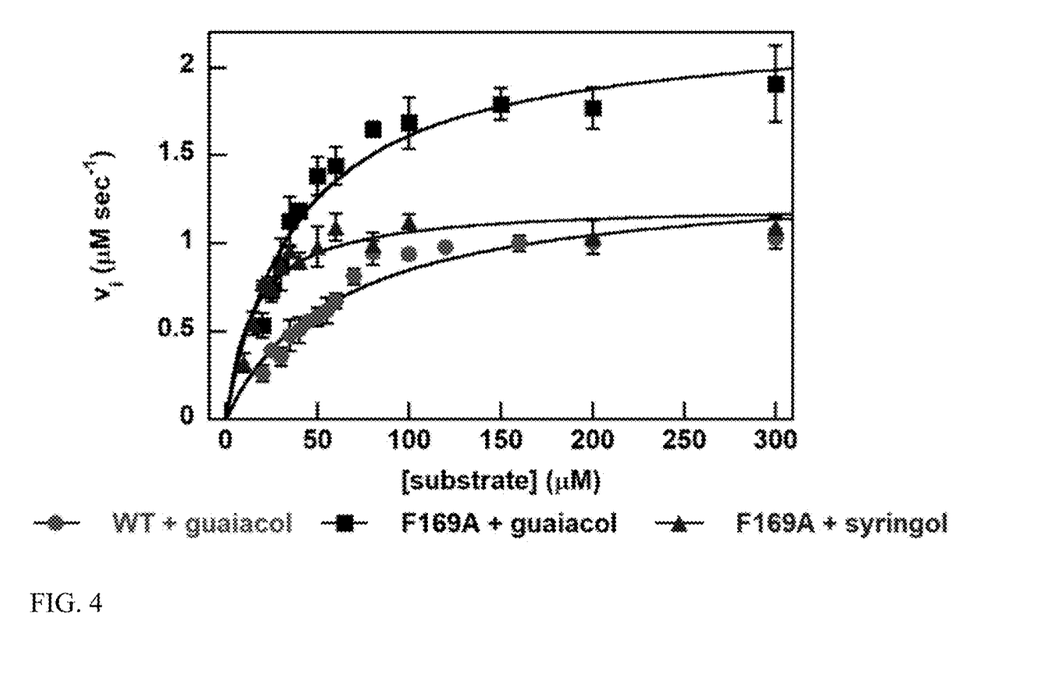
FIG. 4 depicts GcoA-F169A demethylation of both guaiacol and syringol occurs as or more efficiently than with WT GcoA. Initial rate of NADH consumption is plotted with either GcoA-F169A or WT GcoA as catalyst (0.2 µM) and either guaiacol or syringol as the substrate (300 µM NADH, 100 µg catalase, 210 µM $O_2$, 25 mM HEPES, 50 mM NaCl, pH 7.5, 25° C.). The data were fit to the Michaelis-Menton equation. Error bars represent ±1 standard deviation of three or more runs. WT GcoA is unable to demethylate syringol; hence, only guaiacol data are shown.

A broader survey of variants at the GcoA-F169 position confirmed that GcoA-F169A exhibits the best catalytic performance both in terms of specific activity and uncoupling, though other small side chains also permitted reactivity with syringol (Table 1). Steady state kinetic parameters (Table 2, FIG. 4) suggest that GcoA-F169A is a more effective catalyst toward demethylating the first methoxy group of syringol, relative to guaiacol. In particular, the k$_{cat}$/K$_M$ [syringol] is nearly double k$_{cat}$/K$_M$[guaiacol]. Moreover, GcoA-F169A has very slightly improved performance with guaiacol as a substrate relative to the WT enzyme.

Sequence Position 169 in CYP255A Enzymes is Highly Variable

Figure 5A:
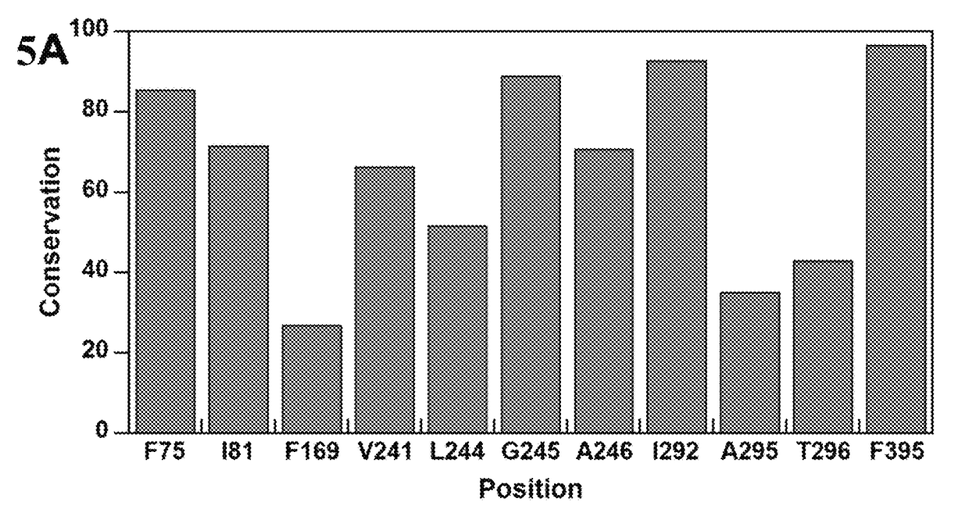
FIG. 5A depicts bioinformatic analysis of CYP255A indicates variability in the 169 position.
Figure 5B:
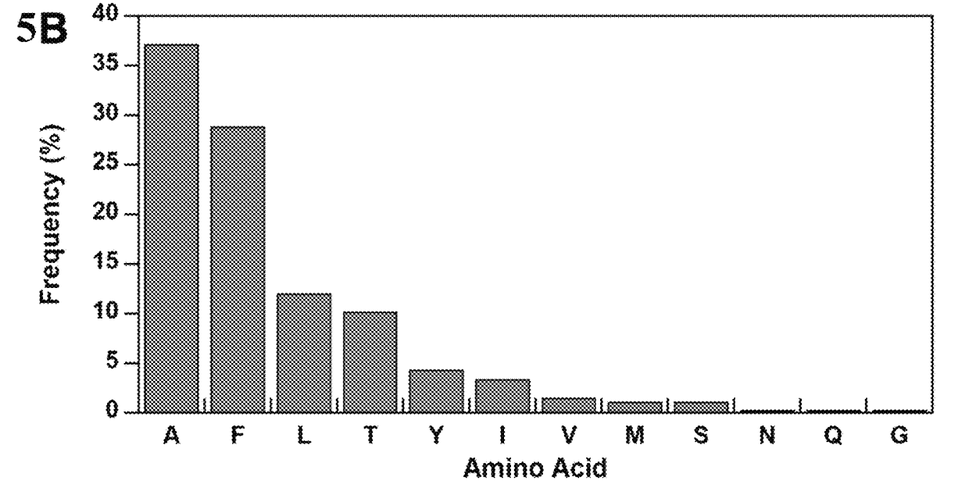
FIG. 5B depicts bioinformatic analysis of CYP255A indicates variability in the 169 position.
Figure 7:
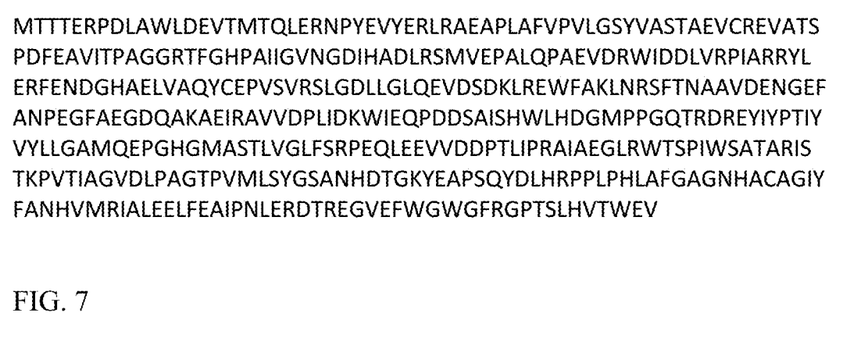
FIG. 7 depicts an embodiment of the amino acid sequence from CYP255A (SEQ ID NO: 1).

Conservation analyses of GcoA homologs revealed a variable 169 position among active site residues. Moreover, not only is GcoA-F169 the least conserved of the triad of phenylalanine residues in the active site, it is also among the least conserved positions in the entire protein (FIG. 5A). From a multiple sequence alignment, we determined that alanine and phenylalanine are the most frequent residues utilized by CYP255A enzymes at position 169 with alanine being more prevalent. In an embodiment, the CYP255A coordinates and sequence used was derived from PDB ID: 5NCB. In another embodiment, the CYP255A amino acid sequence is depicted in FIG. 7. Hence, the GcoA-F169A mutant which showed enhanced turnover on guaiacol and syringol is closer to the CYP255A consensus protein than the WT. It is interesting that although none of the GcoA homologs in our analyses exhibits a histidine at position 169, the GcoA-F169H mutant was stable and showed the highest specific activity on guaiacol. Next to GcoA-F169, A295 and T296 respectively show the highest variability of residues in the active site. Besides these, other residues within 6 Å of the center of mass of the guaiacol substrate generally show high conservation.

The GcoA-F169A in GcoA Enables In Vivo Syringol Utilization

Figure 6A:
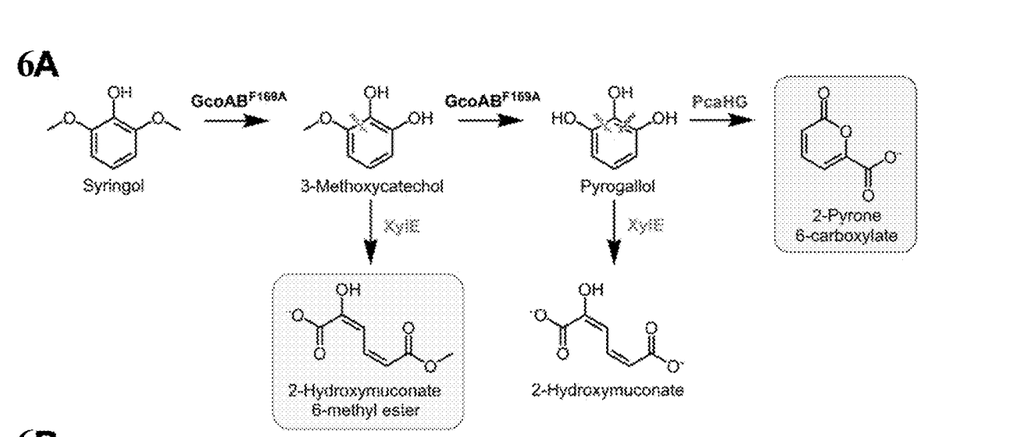
FIG. 6A and FIG. 6B depicts that GcoA-F169A converts syringol in vivo.

In an embodiment, in vivo syringol conversion to pyrogallol using *Pseudomonas putida* KT2440 was demonstrated because it possesses many native aromatic-catabolic pathways relevant to lignin conversion. When jointly expressed with GcoA-F169A and GcoB, we hypothesized that the 2,3-dioxygenase XylE from *P. putida* mt-2 would cleave either 3MC or pyrogallol (FIG. 6A). We evaluated this approach by transforming an empty vector control and plasmids containing the WT GcoAB and GcoA-F169A mutant into *P. putida* AM140, a XylE-overexpressing strain (Table 4). When cultured with 20 mM glucose and 1 mM syringol, cells expressing the GcoA-F169A mutant were completely void of syringol after 6 hours, and instead contained lactonized products of 2-hydroxymuconate 6-methyl ester (FIG. 6B), which was formed via 3MC cleavage. Pyrogallol was not detected, as XylE appears to ring-open 3MC before the second O-demethylation occurs. WT GcoAB also demethylates syringol, but turnover was significantly slower. Syringol conversion was not observed in cells containing an empty vector.

Figure 6B:
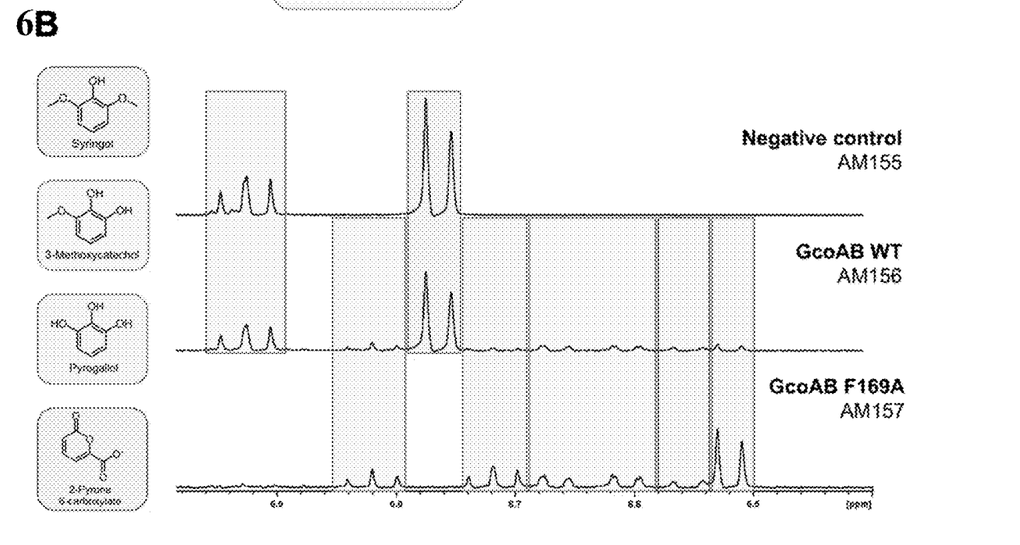

To study the second O-demethylation in vivo, the ring-cleavage mechanism of XylE was substituted with PcaHG, a native 3,4-protocatechuate dioxygenase from *P. putida*, which converts pyrogallol into 2-pyrone-6-carboxylate (FIG. 6A). Again, the WT or GcoA-F169A and GcoB were individually transformed into AM154, which constitutively overexpresses PcaHG (Table 4), and these strains were cultivated as before. After 6 hours, peaks corresponding to syringol completely disappeared in cells expressing GcoA-F169A (AM157), which coincided with the appearance of 3MC, pyrogallol, and 2-pyrone 6-carboxylate (FIG. 6B).

| Strain ID | Genotype | Description of strain construction |
|---|---|---|
| CJ028 | KT2440 ΔcatBCA::Ptac:xylE ΔcatA2 | catBCA was replaced in CJ025 with Ptac:xylE using pCJ005 and this gene replacement was confirmed by diagnostic colony PCR amplification of a 3,078 bp product with primer pair oCJ086/oCJ087. |
| AM140 | KT2440 ΔcatBCA::Ptac:xylE ΔcatA2 ΔpcaHG | CJ028 strain with pcaHG deleted |
| AM142 | KT2440 ΔcatBCA::Ptac:xylE ΔcatA2 ΔpcaHG/pBTL-2 | AM140 transformed with pBTL-2 |
| AM144 | KT2440 ΔcatBCA::Ptac:xylE ΔcatA2 ΔpcaHG/pCJ021 (gcoAB in pBTL-2) | AM140 transformed with pCJ021 |
| AM148 | KT2440 ΔcatBCA::Ptac:xylE ΔcatA2 ΔpcaHG/p0AM27 (gcoAB$_{F169A}$ in pBTL-2) | AM140 transformed with pAM027 |
| CJ612 | KT2440 ΔcatBCA ΔcatA2 | KT2440 strain with in catBCA locus and catA2 deleted |
| AM154 | KT2440 Ptac:pcaHG ΔcatBCA ΔcatA2 | CJ612 strain overexpressing pcaHG |
| AM155 | KT2440 Ptac:pcaHG ΔcatBCA ΔcatA2/pBTL-2 | AM154 transformed with pBTL-2 |
| AM156 | KT2440 Ptac:pcaHG ΔcatBCA ΔcatA2/pCJ021 (gcoAB in pBTL-2) | AM154 transformed with pCJ021 |
| AM157 | KT2440 Ptac:pcaHG ΔcatBCA ΔcatA2/(gcoAB$_{F169A}$ in pBTL-2) | AM154 transformed with pAM027 |

| Plasmid ID | Use | Description of strain construction |
|---|---|---|
| pCJ004 | Deletion of catA2 in KT2440 | Construction of pCJ004 was described previously in Johnson, C. W. & Beckham, G. T. Aromatic catabolic pathway selection for optimal production of pyruvate and lactate from lignin. Metabolic Engineering 28, 240-247 (2015). DOI: 10.1016/j.ymben.2015.01.005 |
| pCJ005 | Replacing catBCA with Ptac-xylE in KT2440 | The 5' targeting region was amplified from *P. putida* KT2440 genomic DNA with primer pair oCJ042/oCJ043 (1,104 bp, which incorporated the tac promoter), xylE (969 bp) was amplified from *P. putida* mt-2 (ATCC 23973) genomic DNA with primer pair oCJ044/oCJ045, and the 3' targeting region was amplified using primer pair oCJ046/oCJ047 (1033 bp). These fragments were then assembled into pCM433 digested with AatII and SacI (7991 bp). |

| | | -continued |
|---|---|---|
| pCJ011 | | Construction of pCJ011 was described previously in Johnson, C. W. & Beckham, G. T. Aromatic catabolic pathway selection for optimal production of pyruvate and lactate from lignin. Metabolic Engineering 28, 240-247 (2015). DOI: 10.1016/j.ymben.2015.01.005 |
| pCJ020 | | Construction of pCJ020 was described previously in Johnson, C. W. & Beckham, G. T. Aromatic catabolic pathway selection for optimal production of pyruvate and lactate from lignin. Metabolic Engineering 28, 240-247 (2015). DOI: 10.1016/j.ymben.2015.01.005 |
| pCJ021 | Episomal expression of gcoAB on pBTL-2 | Construction of pCJ021 was described previously in Tumen-Velasquez, M., et. al. PNAS 83, 201803745-7110. doi: 10.1073/pnas.1803745115 |
| pAM027 | Episomal expression of gcoAB$_{F169A}$ on pBTL-2 | pCJ021 was linearly amplified using oAM173 and oAM174. |
| AM154 | KT2440 Ptac::pcaHG ΔcatBCA ΔcatA2 | CJ612 strain overexpressing pcaHG |
| AM155 | KT2440 Ptac::pcaHG ΔcatBCA ΔcatA2/pBTL-2 | AM154 transformed with pBTL-2 |
| AM156 | KT2440 Ptac::pcaHG ΔcatBCA ΔcatA2/pCJ021 (gcoAB in pBTL-2) | AM154 transformed with pCJ021 |
| AM157 | KT2440 Ptac:pcaHG ΔcatBCA ΔcatA2/(gcoAB$_{F169A}$ in pBTL-2) | AM154 transformed with pAM027 |

Small amounts of pyrogallol and 3MC were also observed with the WT GcoAB (AM156), which correlated to a slight decrease in syringol levels. Pyrogallol or 3MC were not observed in the strain lacking GcoAB (AM155).

Generally, the creation of enzymes that address the challenge of lignin heterogeneity through increased substrate range might come at the cost of reduced activity towards the natural substrate. Unexpectedly, as disclosed herein, not only does GcoA-F169A bind both guaiacol and syringol in a productive orientation analogous to guaiacol in WT, but GcoA-F169A is also more catalytically efficient for O-demethylation of both guaiacol and syringol relative to WT (Table 2). Alongside this biochemical observation, the bioinformatics analysis shows that alanine is the most prevalent residue in the 169 position in the CYP255A family.

As a first step towards enabling syringol catabolism, in vivo experiments as disclosed herein validated in vitro studies by showing efficient O-demethylation of syringol and 3MC via the GcoA-F169 mutant. While 2-pyrone 6-carboxylate was detected, pyrogallol is a poor substrate of PcaHG, as most of the intermediate is lost to oxidation (FIG. 6B). Conversely, XylE rapidly cleaves 3MC forming a dead-end product with minimal substrate loss.

In an embodiment, the mutation of a single residue resulted in efficient turnover of the simplest S-lignin substrate, syringol, which is not efficiently achieved in the WT enzyme.

Methods

Protein expression and purification. Mutagenesis was performed using primers listed in Table 5, with the Q5 polymerase and KLD enzyme mix (NEB) according to the manufacturers protocol. Protein was expressed in Rosetta 2 E. coli (Novagen) and purified by GST-tagged affinity purification before cleavage of the tag and ion exchange before a polishing gel filtration step.

TABLE 5 primer table.

| F169rev | AGCTTGGCGAACCACTCG |
|---|---|
| F169A | GAACCGCTCGgcCACCAACGCC |
| F169H | GAACCGCTCGcaCACCAACGCC |
| F169I | GAACCGCTCGaTCACCAACGC |
| F169L | GAACCGCTCGcTCACCAACGC |
| F169S | GAACCGCTCGTcCACCAACGC |
| F169V | GAACCGCTCGgTCACCAACGC |

Biochemical Characterization

HPLC for product identification and specific activity measurement. HPLC was used to verify the O-demethylated product of GcoA-F169A GcoA/GcoB with guaiacol, syringol, or 3MC. In addition, discontinuous HPLC was used to determine the specific activity of aromatic product disappearance.

Detection of $H_2O_2$ via HRP and Amplex Red assay. A colorimetric assay involving horseradish peroxidase (HRP) and Amplex Red was used to quantify $H_2O_2$ in the reaction between GcoA-F169A GcoA/GcoB, NADH and guaiacol, syringol, or 3MC.

Four hundred eighty-two homologous CYP255A sequences were retrieved from a blastp search against GcoA. After multiple sequence alignment (MSA), conservation was analyzed from relative entropy calculations for each site.

In vivo syringol utilization. Strains used for shake flask experiments were grown overnight in LB media and resuspended the following day in M9 minimal media with 20 mM glucose. Cells were grown until they reached an $OD_{600}$ of about 1, at which point syringol was added at a final concentration of 1 mM. $^1$H NMR spectroscopy was used to analyze syringol consumption.

Mutagenesis

Mutagenesis was performed using the Q5 polymerase and KLD enzyme mix (NEB) according to the manufacturer's instructions. pCJ047 (pGEX-6P-1 vector containing WT GcoA) or pCJ021 (pBTL-2 vector containing WT GcoAB) were used as templates for mutagenesis. All mutants were confirmed by Sanger sequencing.

Protein Expression and Purification

Expression constructs were expressed in *E. coli* Rosetta 2 (DE3) cells (Novagen). Cells were transformed with plasmids containing the GcoA mutant construct and plated out on lysogeny broth (LB) agar containing chloramphenicol (34 mg/L) and carbenicillin (50 mg/L). A single colony was selected and used to inoculate a 20 mL starter culture of LB. After overnight growth at 37° C., 250 rpm, the starter culture was inoculated into 2.5 L flasks containing 1 L of terrific broth (TB) with antibiotics. At an $OD_{600}$ of 1.0, 0.2 mM IPTG was added to induce protein expression. 100 mg/L 5-aminolevulinic acid (GcoA) was added to support productive cofactor incorporation. Induction of protein expression was performed for 16-18 hr at 20° C. with shaking at 250 rpm. Affinity purification was carried out using glutathione-sepharose 4B media (GE Lifesciences) followed by GST-tag cleavage with PreScission protease (GE Lifesciences). Anion exchange chromatography was performed with Source 30Q media (GE Lifesciences) packed into a (GE HR 16/100 Column) with a 10-40% gradient of buffers A (50 mM HEPES pH 7.5, 100 mM NaCl, 1 mM DTT) and B (50 mM HEPES pH 7.5, 1 M NaCl, 1 mM DTT) respectively. For each protein, a final gel filtration step was performed using a HiLoad S200 16/60 pg column (GE Lifesciences) in a buffer containing 25 mM HEPES pH 7.5 and 50 mM NaCl.

Cofactor Analyses

Heme Quantification. To determine the amount of catalytically active heme, CO gas was bubbled into a cuvette containing 1.0-2.5 μM (Pierce BCA assay) F169 GcoA mutants (A, H, S, V, I, L), made up in buffer (25 mM HEPES, 50 mM NaCl, pH 7.5) containing 1.0 mM EDTA, 20% glycerol, 0.5% sodium cholate, and 0.4% non-ionic detergent. Excess sodium dithionite (about 1 mg) was added to reduce the heme iron and the peak attributed to the catalytically competent, ferrous CO-bound heme (about 450 nm) gradually appeared. Several scans were taken to ensure complete binding of CO to heme. A spectrum for a control containing only dithionite-reduced GcoA was measured, and a difference spectrum computed. Absorbances at 420, 450, and 490 nm were recorded to calculate the amount of active GcoA (P450) or inactive GcoA (P420 nm) (see equations 1-3). Reported values are the average of three or more measurements.

$(\Delta A450-\Delta A490)/0.091$=nmol of $P450$ per mL  Equation 1:

$(\Delta A420-\Delta A490)_{observed}-(A450-A490)_{theoretical}]/$
$0.110$=nmol of cytochrome $P420$ per mL  Equation 2:

nmol of $P450$ per mL×(−0.041)=
$(\Delta A420-A4901)_{theoretical}$  Equation 3:

Here, ΔA450 and ΔA420 are the differences between the reference and sample spectra at absorbances 450 and 420 nm, respectively.

Determination of [FAD] and Non-Heme [Fe] in GcoB

FAD was released from GcoB by denaturing 200 μL of a protein (0.024 μM) solution with 5 μL saturated ammonium sulfate, pH 1.4 (7% v/v $H_2SO_4$). Precipitated protein was pelleted by centrifugation and the UV/vis spectrum of the FAD-containing supernatant was measured. The absorbance at 454 nm, $\varepsilon_{FAD}$=11.3 $mM^{-1}$ $cm^{-1}$, and total protein concentration determined by the BCA assay (Pierce) were used to determine the concentration of FAD bound to GcoB. An extinction coefficient for GcoB-bound FAD was estimated via the slope of a line relating absorbance at 454 nm to the concentration of GcoB-FAD.

To determine the Fe—S content of GcoB, the protein was first denatured. Fifty μL of supernatant was added to 25 μL of 5% w/v sodium ascorbate to reduce the iron. One hundred μL of bathophenanthroline disulfonate (0.1% w/v in $ddH_2O$) was added and the sample was incubated for 1 h. The resulting Fe(II) complex was quantified via its absorbance at 535 nm ($\varepsilon_{535}$=22.14 $mM^{-1}$ $cm^{-1}$, determined using $FeSO_4$ standards). An extinction coefficient for GcoB-bound 2Fe—2S cluster was estimated via the slope of a line relating absorbance at 423 nm to [GcoB—2Fe—2S].

Steady State Kinetics and Substrate Dissociation Constants

Steady state kinetics of F169A. 0.2 μM each of F169A GcoA and GcoB were dissolved in air-saturated buffer (25 mM HEPES, 50 mM NaCl) in a cuvette at pH 7.5, 25° C. 100 μg/mL catalase was added to each reaction to capture any $H_2O_2$ formed during the uncoupled reaction. A saturating amount of NADH (≥5 $K_M$, 300 μM) was added and a background rate of NADH oxidation in air (about 210 μM $O_2$) recorded via continuous scanning of the UV/vis spectrum (Varian Cary 50). 20-300 μM guaiacol or syringol 2-20 mM stock dissolved in DMSO was added and the reaction was monitored via measurement of UV/vis spectra for several minutes. The initial velocity was determined by disappearance of the characteristic NADH absorbance at 340 nm ($\varepsilon_{344}$=6.22 $mM^{-1}$ $cm^{-1}$). A plot of $v_i$ versus the concentration of guaiacol was fit to equation 4 to obtain $k_{cat}$, $K_M$, and $k_{cat}/K_M$. For specific activity determination, the above method was used but with saturating (300 μM) guaiacol, syringol, or 3-methoxycatechol (3MC), and in the presence of all F169 GcoA mutants (A, H, S, V, I, L). The linear portion of the concentration of NADH versus time was fit and referenced to the amount of GcoA used (0.2 μM). Reported values are the average of at least 3 measurements and reported errors are standard deviations.

$v_i=V_{max}[S]/(K_M+[S])$  Equation (4):

Determination of Substrate Dissociation Constants ($K_D$) with F169A

Zero to 60 μM of guaiacol, syringol, or 3MC in 0.5 or 1 μM aliquots, were titrated into a cuvette containing 3 μM F169A GcoA in 25 mM HEPES, 50 mM NaCl, pH 7.5. The spectrum after each substrate addition was recorded, beginning with no substrate bound. The solution reached equilibrium before the next addition. A difference spectrum was made to illustrate the shift from a low-spin aquo-heme complex to the high-spin substrate-bound complex (spectral shift from 417 nm to 388 nm). The resulting difference spectra showed a peak at 388 nm, and a trough at 417 nm. The absorbance at 388 nm ($AbS_{388-417\ nm}$) was plotted as a function of [substrate], yielding a quadratic curve that was fit to equation (5) to determine the $K_D$.

$$\Delta Abs_{obs} = \frac{\Delta Abs_{max}}{2E_t}\left(L_0 + E_t + K_D - \sqrt{(L_0 + E_t + K_d)^2 - 4E_t * L_0}\right) \quad \text{Equation (5)}$$

Where $L_0$, $E_t$, $K_D$, and $\Delta Abs_{max}$ are the ligand concentrations, total protein (subunit) concentration, the equilibrium dissociation constant, and the maximum $AbS_{388-417nm}$, respectively. Reported values are the average of 2 or more measurements.

Product Analysis

Formaldehyde determination. A colorimetric assay using tryptophan can be used to quantify the amount of formaldehyde produced in F169 GcoA/B reactions with guaiacol, syringol, or 3MC. 0.2 μM each of F169 GcoA mutants and GcoB were dissolved in air-saturated buffer (25 mM HEPES, 50 mM NaCl) in a cuvette at pH 7.5, 25° C. 100 μg/mL catalase was added to each reaction to capture any $H_2O_2$ formed during the uncoupled reaction. Two hundred μM NADH was added and the background rate recorded. One hundred (guaiacol, syringol, or 3MC) or 200 (syringol) μM of substrate was then added and the reaction monitored until there was no more change, due to either substrate, NADH or $O_2$ depletion, whichever occurred first. 200 μL of the reaction was then quenched by adding 200 μL of a 0.1% tryptophan solution in 50% ethanol and 200 μL of 90% sulfuric acid. Upon thorough mixing, 40 μL of 1% $FeCl_3$ was added. The solution was then incubated in a heating block for 90 min at 70° C. After cooling, the absorbance was read at 575 nm and the concentration of formaldehyde was calculated by using $\varepsilon_{575\ nm}$=4.2 $mM^{-1}$ $cm^{-1}$, obtained with formaldehyde as a standard. A negative control included everything but the substrate and was used as a baseline.

HPLC for Product Identification and Specific Activity Measurement

Analyte analysis of the above end-point reactions (100 μM guaiacol, syringol, or 3MC, or 200 μM syringol) was performed on an Agilent 1100 LC system (Agilent Technologies) equipped with a G1315B diode array detector (DAD). Each sample and standard was injected at a volume of 10 μL onto a Symmetry C18 column 5 μm, 4.6×150 mm column (Waters). The column temperature was maintained at 30° C. and the buffers used to separate the analytes of interest was 0.01% TFA in water (A)/acetonitrile (B). The separation was carried out using a gradient program of: (A)=99% and (B)=1% at time t=0 min; (A)=99% and (B)=1% at time t=2 min, (A)=50% and (B)=50% at t=8 min; (A)=1% and (B)=99% at t=8.01 min; (A)=99% and (B)=1% at t=10.01 min; (A)=99% and (B)=1% at t=11 min. The flow rate was held constant at 1.5 mL $min^{-1}$, resulting in a run time of 11 minutes. DAD wavelengths of 210 and 325 nm were used for analysis of the analytes of interest. Standard curves were generated using 0-500 μM of guaiacol, syringol, 3MC, catechol, and pyrogallol. Integrated intensities vs [standards] were plotted and the resulting standard curves used to quantify the reactants and products.

For specific activity determination, 300 μM guaiacol, syringol, or 3MC were added from 0.1 M DMSO stocks to air saturated buffer (25 mM HEPES, 50 mM NaCl, pH 7.5), with a final volume of 1 mL. The concentration of analyte was measured via the above HPLC method. Then, 0.2 μM F169A/GcoB and 100 μg/mL catalase were added. Upon addition of 300 μM NADH, the timer was started and 50 μL removed every 10 (guaiacol and syringol) or 30 (3MC) seconds. The reaction of each aliquot was immediately quenched with 12.5 μL saturated ammonium sulfate, 7% v/v $H_2SO_4$ (pH 2.0) prior to loading onto the HPLC column. The concentration of substrate disappearance was referenced to GcoA (0.2 μM) and fit to a linear line to determine specific activity.

Uncoupling Reactions

Detection of $H_2O_2$ via horseradish peroxidase (HRP) and Amplex Red assay. The reaction between 100 μM guaiacol or 3MC with 0.2 μM F169A/GcoB and 100 μM NADH in air-saturated buffer (25 mM HEPES, 50 mM NaCl, pH 7.5) was monitored continuously in a quartz cuvette, using the NADH consumption assay described above. The same thing was done for syringol, but with either 100 or 200 μM NADH. When there was no longer any change in the spectra, e.g., the reaction was completed, 100 μL was removed from the cuvette and pipetted into a 96-well microplate. A 5 mL solution containing 50 μL of 10 mM Amplex Red (prepared in DMSO and stored at −20° C.) and 100 μL of 10 U/mL HRP was made up in the above buffer. One hundred μL of this was added to each of the wells with each reaction sample. The plate was incubated in the dark at room temperature for 30 min, at which point the absorbance at 572 nm was recorded by a Varioskan Lux microplate reader (Thermo Scientific). The absorbance was compared to a standard curve with 0-100 μM $H_2O_2$ to quantify the amount of peroxide produced in the reactions.

Crystallography

Purified protein was buffer exchanged into 10 mM HEPES pH 7.5 and concentrated to an A280 value of 12, as measured on a NanoDrop 2000 spectrophotometer (Thermo Fisher). Crystals of GcoA were grown with 2.4 M sodium malonate and 200 mM substrate, dissolved in 40% DMSO where necessary. Crystals were cryocooled directly in liquid $N_2$ without further addition of cryoprotectants. All data were collected at Diamond Light Source (Harwell, UK). For each crystal, 1800 images were taken at 0.1° increments using the default wavelength of 0.9795 Å on beamline i04. Data was captured on a Pilatus 6M-F detector. All phases were solved by molecular replacement from the original WT GcoA structure in complex with guaiacol with all non-polypeptide components removed. Data were processed, phased, and models were built and refined using Xia2 and the Phenix suite.

What is claimed is:

1. A non-naturally occurring GcoAB enzyme comprising the amino acid sequence of SEQ ID NO: 1 capable of the O-aryl-demethylation of syringol and the O-aryl-demethylation of guaiacol and wherein a phenylalanine residue at the active site has been changed to an amino acid selected from the group consisting of alanine, serine, histidine, valine, isoleucine, and leucine.

2. The enzyme of claim 1 wherein a phenylalanine at the active site has been changed to alanine.

3. The enzyme of claim 1 comprising a $k_{cat}$ for guaiacol of at least 11 sec$^{-1}$ and a $k_{cat}$ for syringol of at least 5.9 sec$^{-1}$.

4. The enzyme of claim 1 comprising a $K_M$ for guaiacol of less than about 40 mM and a $K_M$ for syringol of less than about 10 mM.

5. The enzyme of claim 1 comprising a kcat/$K_M$ for guaiacol of greater than about 290 mM$^{-1}$ sec$^{-1}$ and a kcat/$K_M$ for syringol of greater than about 600 mM$^{-1}$ sec$^{-1}$.

6. The enzyme of claim 1 comprising increased specific activity for guiaicol when compared to the native GcoAB enzyme.

7. The enzyme of claim 1 wherein the specific activity for syringol is greater than 0.54 μmol sec$^{-1}$ μmol$^{-1}$.

8. The enzyme of claim 1 wherein the specific activity for syringol is greater than 3.9 μmol sec$^{-1}$ μmol$^{-1}$.

9. The enzyme of claim 1 wherein the specific activity for syringol is greater than 5.1 μmol sec$^{-1}$ μmol$^{-1}$.

* * * * *